United States Patent [19]

Tanaka et al.

[11] Patent Number: 5,109,003
[45] Date of Patent: Apr. 28, 1992

[54] METHOD FOR THE TREATMENT OF PEPTIC ULCER DISEASE

[75] Inventors: Toshizo Tanaka, Kawagoe; Shoryo Hayashi, Tokorozawa; Yuko Morioka, Sakado, all of Japan; Ulrich Gebert, Kelkheim/Taunus,, Fed. Rep. of Germany

[73] Assignee: Hoechst Japan Limited, Tokyo, Japan

[21] Appl. No.: 566,756

[22] Filed: Aug. 14, 1990

[30] Foreign Application Priority Data

Aug. 16, 1989 [JP] Japan .................................. 1-210187

[51] Int. Cl.$^5$ ..................... A61K 31/52; C07D 473/02
[52] U.S. Cl. ...................................... 514/263; 544/267
[58] Field of Search .......................... 544/277; 514/263

[56] References Cited

U.S. PATENT DOCUMENTS 4,833,146  5/1989  Gebert et al. ..................... 514/263
4,845,102  7/1989  Sakurai et al. ..................... 514/263

Primary Examiner—Diana G. Rivers
Attorney, Agent, or Firm—Finnegan, Henderson, Farabow, Garrett and Dunner

[57] ABSTRACT

Therapeutic agents for the treatment of peptic ulcer disease, containing as active ingredient, at least one compound of the general formula I

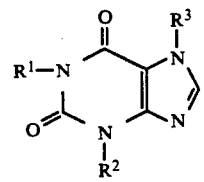

wherein one of $R^1$ and $R^3$ is

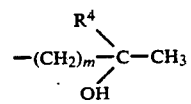

(wherein m is 1–5, $R^4$ represents a ($C_1$–$C_4$)alkyl group); the other one of $R^1$ and $R^3$ is hydrogen, ($C_3$–$C_6$)alkenyl or ($C_1$–$C_8$)alkyl which can be substituted with up to 2 hydroxyl groups or a ($C_1$–$C_4$)alkoxy group; and $R^2$ is ($C_1$–$C_4$)alkyl.

9 Claims, No Drawings

METHOD FOR THE TREATMENT OF PEPTIC ULCER DISEASE

BACKGROUND OF THE INVENTION (1) Field of the Invention

This invention relates to pharmaceuticals suitable for use in the treatment of peptic ulcer disease. Peptic ulcer is an ulceration of the mucous membrane of the stomach and/or duodenum; the mucous membrane is damaged by the action of hydrochloric acid and pepsin due to its decreased resistance to the aggressive factors induced by various causes including physical and psychological stress.

(2) Problems to Be Solved by the Invention

Until recently, sodium bicarbonate and aluminum compounds had been used to neutralize gastric acid as aggressive factor. The drugs commonly used now to treat peptic ulcer disease include anticholinergics, gastroprotective agents, drugs improving mucosal blood flow, and $H_2$-receptor antagonists.

Drugs for peptic ulcers are administered for a long period of time and are required to have the fewest adverse effects as well as high efficiency. However, the available drugs are not necessarily satisfactory in safety and efficacy. In addition there is another problem associated with the use of the drug, namely, the relapse of ulcer after drug treatment is stopped. For example, the $H_2$-receptor antagonists are very effective in improving gastric and duodenal ulcers by inhibiting gastric acid secretion but ulcers recur at high incidence after discontinuing treatment with the drugs.

On the other hand, pentoxifylline, the compound of the general formula I where in $R^1$ is 5-oxohexyl and $R^2$ and $R^3$ are methyl has already been reported by Vorobyev and Samsonov to have antiulcer effects (Ter. Arkh. 57, 52–55, 1985). Moreover, it has been described in Japanese Laid-Open Patent Publication 225317/88 that the compounds represented by the general formula I wherein $R^1$ is 4-oxopentyl or 5-oxohexyl, $R^2$ is methyl or ethyl and $R^3$ is $C_2$–$C_4$ alkyl have antiulcer effect superior to that of pentoxifylline.

As a result of our extensive studies for superior therapeutics for peptic ulcer disease, we have found that specific xanthine derivatives have high efficiency and safety enough to be new drugs suitable for use in the treatment of the disease, inclusive of irritations of the gastro-intestinal mucosa caused by drugs such as non-steroidal anti-inflammatory agents.

DETAILED DESCRIPTION OF THE INVENTION

Thus, the present invention provides therapeutic agents for the treatment of peptic ulcer disease containing, as active ingredient, at least one compound of the general formula I

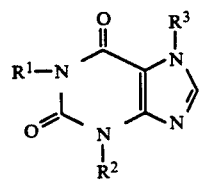

wherein one of $R^1$ and $R^3$ is

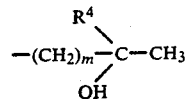

(wherein m is 1–5, $R^4$ represents a ($C_1$–$C_4$)alkyl group); the other one of $R^1$ and $R^3$ is hydrogen, ($C_3$–$C_6$)alkenyl or ($C_1$–$C_8$)alkyl which can be substituted with up to 2 hydroxyl groups or a ($C_1$–$C_4$)alkoxy group; and $R^2$ is ($C_1$–$C_4$)alkyl.

In this context, those therapeutic agents are preferred which contain at least one compound of the formula I in which one of $R^1$ and $R^3$ denotes

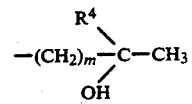

(wherein m is 3, 4 or 5 and $R^4$ represents methyl or ethyl); the other one of $R^1$ and $R^3$ denotes hydrogen, ($C_3$–$C_4$)alkenyl or ($C_1$–$C_4$)alkyl optionally substituted with up to 2 hydroxyl groups or a ($C_1$–$C_2$)alkoxy group; and $R^2$ represents methyl or ethyl.

A further preferred embodiment of the invention relates to therapeutic agents which contain at least one of those compounds of the formula I in which one of $R^1$ and $R^3$ denotes

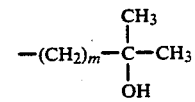

(wherein m is 4 or 5); the other one of $R^1$ and $R^3$ represents ($C_1$–$C_4$)alkyl or optionally substituted with a ($C_1$–$C_2$)alkoxy group and $R^2$ is ethyl.

Among these therapeutic agents, those in turn are particularly preferred which contain at least one of those compounds of the formula I in which $R^1$ denotes

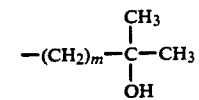

(wherein m is 4 or 5); $R^3$ represents ($C_1$–$C_4$)alkyl or optionally substituted with a ($C_1$–$C_2$)alkoxy group and $R^2$ is ethyl.

The invention also relates to novel trisubstituted xanthine derivatives of the formula I, in which $R^2$ denotes ethyl;

where a)

$R^1$ denotes 6-hydroxy-6-methylheptyl and $R^3$ represents ethyl, propyl or isopropyl;

or b)

$R^1$ denotes 5-hydroxy-5-methylhexyl and $R^3$ represents ethyl or butyl.

A further embodiment of the invention concerns novel xanthine compounds of the formula I, in which one of $R^1$ and $R^3$ denotes

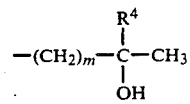

(wherein m is an integer of 1–5 and $R^4$ represents a $(C_1-C_4)$alkyl group);
the other one of
$R^1$ and $R^3$ denotes $(C_3-C_6)$alkenyl; and
$R^2$ represents $(C_1-C_4)$alkyl;
excluding 7-(3-butenyl)-1-(5-hydroxy-5-methylhexyl)-3-methylxanthine.

The invention relates in particular to xanthine derivatives of the formula I in which one of $R^1$ and $R^3$ denotes

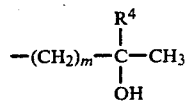

(wherein m is an integer of 3, 4 or 5 and $R^4$ represents methyl or ethyl); the other one of $R^1$ and $R^3$ denotes $(C_3-C_4)$alkenyl; and $R^2$ represents methyl or ethyl; excluding 7-(3-butenyl)-1-(5-hydroxy-5-methylhexyl)-3-methylxanthine.

Xanthine derivatives of the formula I are particularly preferred in which one of $R^1$ and $R^3$ denotes

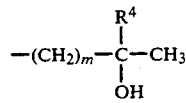

(wherein m is an integer of 4 and $R^4$ represents methyl); the other one of $R^1$ and $R^3$ denotes allyl or butenyl; and $R^2$ represents methyl or ethyl; excluding 7-(3-butenyl)-1-(5-hydroxy-5-methylhexyl)-3-methylxanthine.

The compounds used as active ingredient are characterized by their tertiary hydroxyalkyl group and differ in this point from xanthine derivatives having an oxoalkyl group whose antiulcer activity has been reported. These compounds are effective for the treatment of ulcer caused by necrotizing substances such as ethanol and caused by stress, especially effective to stress ulcer.

The compounds used as active ingredients in this invention are prepared according to methods described in Japanese laid open Patent Application (JP-LOP) 501149/88 corresponding to European Patent 268 585. The novel compounds are prepared by routine methods from known compounds in analogy to the methods described, for example in the before-mentioned JP-LOP or also in the international application published under the Patent Cooperation Treaty WO 87/00523. A convenient method is the introduction of $R^1$ by alkylation. The alkylation is carried out by reacting a compound of the formula I wherein $R^1$ or $R^3$ is hydrogen with an alkylating agent such as $R^1$-halogen under alkaline conditions.

Somewhat more detailed, the novel trisubstituted xanthine derivatives of the formula I, in which $R^2$ denotes ethyl, and where a) $R^1$ denotes 6-hydroxy-6-methylheptyl and $R^3$ represents ethyl, propyl or isopropyl, or
b) $R^1$ denotes 5-hydroxy-5-methylhexyl and $R^3$ represents ethyl or butyl are prepared by reacting a compound of the formula II

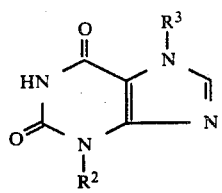

in which $R^2$ and $R^3$ have the meaning as defined above in the presence of a basic agent or in form of a salt, is then alkylated with the alkylating agent $R^1$—X, in which $R^1$ has the meaning as defined above and X denotes halogen, a sulfonic acid ester or phosphonic acid ester to give a compound of the formula I.

The invention also relates to a process as defined above characterized in that a compound of the formula I is prepared, in which one of $R^1$ and $R^3$ denotes

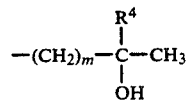

(wherein m is an integer of 1–5 and $R^4$ represents a $(C_1-C_4)$alkyl group); the other one of $R^1$ and $R^3$ denotes $(C_3-C_6)$alkenyl; and $R^2$ represents $(C_1-C_4)$alkyl; excluding 7-(3-butenyl)-1-(5-hydroxy-5-methylhexyl)-3-methylxanthine.

The reaction of the disubstituted xanthine derivatives II, respectively, with the alkylating agents is usually carried out in a dispersing agent or solvent which is inert towards the participants in the reaction. Possible dispersing agents or solvents are, in particular, dipolar aprotic solvents, for example formamide, dimethylformamide, dimethylacetamide, N-methylpyrrolidone, tetramethylurea, hexamethylphosphoric acid triamide, dimethyl sulfoxide, acetone and butanone; however, it is also possible to use alcohols, such as methanol, ethylene glycol and mono- or dialkyl ethers thereof, in which the alkyl group has 1 to 4 carbon atoms but both together have not more than 5 carbon atoms, ethanol, propanol, isopropanol and the various butanols; hydrocarbons, such as benzene, toluene or xylenes; halogenated hydrocarbons, such as methylene chloride or chloroform; pyridine and mixtures of the solvents mentioned or mixtures thereof with water.

The alkylation ractions are advantageously carried out in the presence of a basic condensing agent. Agents which are suitable for this are, for example, alkali metal or alkaline earth metal hydroxides, carbonates, hydrides and alcoholates, and organic bases such as trialkylamines (for example triethyl- or tributylamine), quaternary ammonium or phosphonium hydroxides and cross-linked resins with fixed, optionally substituted ammonium or phosphonium groups. However, the xanthine derivatives can also be employed in the alkylation reaction directly in the form of their separately prepared salts, for example the alkali metal, alkaline earth metal or optionally substituted ammonium or phosphonium salts. The disubstituted xanthine compounds can moreover be conveniently alkylated both in the presence of the abovementioned inorganic condensing agents and in the form of their alkali metal or alkaline earth metal salts with the aid of so-called phase transfer catalysts, for example tertiary amines, quaternary ammonium or phosphonium salts or crown ethers, preferably in a two-phase system under the conditions of phase transfer catalysis. Suitable phase transfer catalysts, which are mostly commercially available, are, inter alia, tetra($C_1$-$C_4$)-alkyl- and methyltrioctylammonium and -phosphonium salts, methyl-, myristyl-, phenyl- and benzyl-tri($C_1$-$C_4$)alkyl- and cetyltrimethylammonium salts and ($C_1$-$C_{12}$)alkyl- and benzyl-triphenylphosphonium salts, as a rule those compounds which have the cation which is larger and of more symmetric structure proving to be more effective.

The introduction of the radical $R^1$ by the procedures described above is in general carried out at a reaction temperature between 0° C. and the boiling point of the particular reaction medium used, preferably between 20° C. and 130° C., if appropriate under increased or reduced pressure, but usually under atmospheric pressure, it being possible for the reaction time to be from less than one hour to several hours.

The therapeutic agents are prepared by bringing at least one compound of the formula I—advantageously together with at least one usual carrier and/or excipient—into a suitable form for administration.

Possible administration routes of the compounds of this invention are oral, intravenous, subcutaneous, intramuscular, and rectal. The clinical dose is about 100-900 mg/60 kg body weight, preferably about 300-600 mg/60 kg body weight. Usable dosage forms are tablets, sugar-coated tablets, pills, capsules, powders, granules, suppositories, and injections. The tablets, sugar-coated tablets, capsules, and granules are desirable for oral, the injections for parenteral, and the suppositories for rectal administration.

The compounds of this invention can be used each as a monopharmacon or as a combination or in combination with other agents for the treatment of peptic ulcer disease including antacids.

For injection, the powder for injection is usable. In this case, the compounds of this invention are dissolved in water containing one or more adequate water-soluble excipients such as mannitol, sucrose, lactose, maltose, glucose, and fructose. Then the solution is put into the vial or ampule, which is sealed after lyophilization of the contents.

For oral administration, an enteric-coated preparation is possible in addition to the dosage forms listed above. In this case, the tablets, granules, or fine granules are prepared using the following as additives as required: excipients such as mannitol, sucrose, lactose, maltose, starch, silica, and calcium phosphate; lubricants such as talc and magnesium stearate; binders such as sodium carboxymethylcellulose, methylcellulose, gelatin, and gum arabic; and disintegrating aids such as calcium carboxymethylcellulose. Then, the tablets, granules, or fine granules are coated with one or more enteric bases with, if required, a coloring agent such as titanium dioxide. The bases for enteric coating include cellulose acetate phthalate, hydroxypropylmethylcellulose phthalate, hydroxypropylmethylcellulose acetylsuccinate, polyvinyl alcohol phthalate, styrene-maleic anhydride copolymers, styrene-maleic acid copolymers, methyl methacrylate-, methacrylic acid copolymers, and methyl acrylatemethacrylic acid copolymers. The enteric-coated granules or fine granules are preferably filled into capsules.

Enteric-coated capsules can be obtained by coating capsules manufactured by a conventional method with one or more of the enteric bases listed above or by manufacturing capsules with an enteric base alone or in a mixture with gelatin.

Suppositories can be prepared as follows. The compounds of this invention are mixed homogenously with (a) a lipophilic base such as cacao butter or adeps solidus in various proportions or (b) a hydrophilic base such as polyethylene glycol or glycerol. The mixture containing the compounds of this invention is put into molds.

The weight ratio of the active ingredient(s) of the formula I and the respective carrier or excipient can vary within a very wide, range; preferably it is within the range of about 1:100 to about 100:1.

The antiulcer effects and the toxicological Profile of the compounds of this invention were as follows. The compounds tested are shown in Table 1. Propentofylline=1-(5'-oxohexyl)-3-methyl-7-propyl xanthine, whose antiulcer activity is described in Japanese Laid-Open Publication 225317/88 and superior to that of pentoxifylline, was used as a reference drug for the pharmacological studies.

TABLE 1

Compounds of formula I (known and novel)

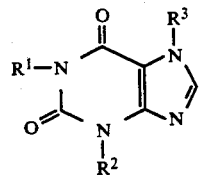

| Compound No. | $R^1$ | $R^2$ | $R^3$ |
|---|---|---|---|
| 1 | CH₃—C(OH)(CH₃)—(CH₂)₄— | —C₂H₅ | —(CH₂)₂—CH₃ |
| 2 | " | " | —CH₃ |
| 3 | CH₃—C(OH)(CH₃)—(CH₂)₃— | " | —(CH₂)₂—CH₃ |
| 4 | CH₃—C(OH)(CH₃)—(CH₂)₅— | —C₂H₅ | —CH₃ |
| 5 | CH₃—C(OH)(CH₃)—(CH₂)₄— | —CH₃ | —H |
| 6 | " | " | —(CH₂)₂—CH=CH₂ |
| 7 | CH₃—C(OH)(CH₃)—(CH₂)₄— | " | —CH₃ |
| 8 | CH₃—(CH₂)₂— | " | —(CH₂)₄—C(OH)(CH₃)—CH₃ |

TABLE 1-continued

Compounds of formula 1 (known and novel)

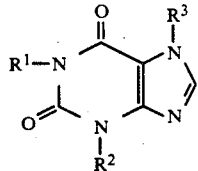

| Compound No. | R¹ | R² | R³ |
|---|---|---|---|
| 9 | CH₃−C(CH₃)(OH)−(CH₂)₄ | −CH₃ | −(CH₂)₂−CH(OH)−CH₂(OH) |
| 10 | CH₃−CH₂−O−(CH₂)₂ | " | −(CH₂)₄−C(CH₃)(OH)−CH₃ |
| 11 | CH₃−C(CH₃)(OH)−(CH₂)₅− | " | −(CH₂)₂−CH₃ |
| 12 | CH₃−CH₂−C(CH₃)(OH)−(CH₂)₄ | " | −(CH₂)₂−CH₃ |
| 13 | CH₃−C(CH₃)(OH)−(CH₂)₅− | −C₂H₅ | −C₂H₅ |
| 14 | " | " | −(CH₂)₂−CH₃ |
| 15 | " | " | −CH(CH₃)−CH₃ |
| 16 | CH₃−C(CH₃)(OH)−(CH₂)₄− | " | −C₂H₅ |
| 17 | " | " | −(CH₂)₃−CH₃ |
| 18 | " | " | −CH₂−O−CH₂−CH₃ |
| 19 | " | " | −CH₂−CH=CH₂ |
| 20 | " | −CH₃ | " |
| 21 | CH₂=CH−(CH₂)₂− | −C₂H₅ | −(CH₂)₄−C(CH₃)(OH)−CH₃ |
| 22[a] | CH₃−C(O)−(CH₂)₄ | " | −(CH₂)₂−CH₃ |

[a]Reference compound (propentofylline)

1. ANTIULCER EFFECTS

1.1. Protective Effect of Gastric Ulcer Induced by Restraint Plus Water-immersion Stress in Rats Male Sprague-Dawley rats weighing 250–300 g were used in groups of 5–35. The animals were given the compounds by the oral route after fasting overnight. Immediately, under light ether anesthesia they were placed in a restraint box and immersed in water at 23° C. for 6 or 7 hours. Then the animals were sacrificed, and their stomachs were isolated, inflated with 8 ml of 1% formalin for 10 minutes, opened along the greater curvature, and examined for the presence of gastric erosions. The longest axis of each erosion induced on the glandular section of the stomach was measured, and the sum of the lengths was defined as an ulcer index. The results are shown in Table 2.

TABLE 2

Protective effect on stress-induced gastric ulcer in rats

| Compound | Dose (mg/kg, p. o.) | No. of animals | Ulcer index (mm) | Inhibition (%) |
|---|---|---|---|---|
| Control (Distilled water) | 0 | 35 | 26.0 ± 2.2 | — |
| 1 | 10 | 5 | 8.7 ± 1.6** | 66.5 |
| 2 | 10 | 5 | 6.5 ± 1.6** | 75.0 |
| 3 | 10 | 5 | 12.8 ± 2.5* | 50.8 |
| 4 | 10 | 5 | 10.6 ± 1.8* | 59.2 |
| 5 | 10 | 5 | 7.5 ± 2.0** | 71.2 |
| 7 | 10 | 5 | 15.8 ± 4.4 | 39.2 |
| 8 | 10 | 5 | 12.1 ± 2.9* | 53.5 |
| 9 | 10 | 5 | 17.8 ± 3.3 | 31.5 |
| 10 | 10 | 5 | 17.8 ± 3.3 | 31.5 |
| 11 | 10 | 5 | 16.0 ± 3.8 | 38.5 |
| 13 | 10 | 5 | 5.0 ± 1.0** | 80.8 |
| 16 | 10 | 6 | 6.8 ± 1.6** | 73.8 |
| 18 | 10 | 5 | 6.9 ± 2.1* | 73.5 |
| 19 | 10 | 9 | 10.2 ± 2.4 | 60.8 |
| 20 | 10 | 5 | 10.6 ± 3.0 | 59.2 |
| 22[a] | 10 | 5 | 18.4 ± 3.0 | 29.2 |
| Control (10% EtOH) | 0 | 19 | 32.9 ± 3.3 | — |
| 6 | 10 | 5 | 17.4 ± 4.5* | 47.1 |
| 14 | 10 | 5 | 4.8 ± 1.7** | 85.4 |
| 15 | 10 | 5 | 6.6 ± 1.6** | 79.9 |
| 17 | 10 | 5 | 12.5 ± 3.3** | 62.0 |

[a]Reference compound (propentofylline)
**$P < 0.01$, *$P < 0.05$ (P = significance)
Each value represents the means ± S. E. (standard error)

1.2. Protective Effect on Ethanol-induced Gastric Ulcer in Rats

Male Sprague-Dawley rats weighing 300–400 g were used in groups of 4–36. After fasting overnight, the animals were given orally the compounds. Thirty minutes later they received absolute ethanol (1 ml/body) orally and were sacrificed after 60 minutes. The stomach was removed and examined for erosions. The ulcer index was obtained in the same way as under 1.1. The results are shown in Table 3.

TABLE 3

Protective effect on ethanol-induced gastric ulcer in rats

| Compound | Dose (mg/kg, p. o.) | No. of animals | Ulcer index (mm) | Inhibition (%) |
|---|---|---|---|---|
| Control (Distilled water) | 0 | 36 | 93.1 ± 8.9 | — |
| 1 | 10 | 4 | 12.0 ± 6.9** | 87.1 |
| 2 | 10 | 5 | 23.5 ± 7.0** | 74.8 |
| 4 | 10 | 5 | 21.2 ± 8.4** | 77.2 |
| 12 | 10 | 5 | 26.1 ± 10.8** | 72.0 |
| 13 | 10 | 5 | 15.7 ± 9.4** | 83.1 |
| 16 | 10 | 5 | 17.0 ± 7.1* | 81.7 |
| 18 | 10 | 5 | 16.8 ± 7.1** | 82.0 |
| 19 | 10 | 5 | 5.2 ± 2.0 | 94.4 |
| 21 | 10 | 5 | 19.2 ± 9.2 | 79.4 |
| Control 10% EtOH | 0 | 33 | 78.9 ± 8.5 | |
| 14 | 10 | 5 | 3.7 ± 1.1** | 95.3 |
| 15 | 10 | 5 | 4.2 ± 2.2** | 94.7 |
| 17 | 10 | 5 | 13.0 ± 8.3* | 83.5 |

TABLE 3-continued

Protective effect on ethanol-induced gastric ulcer in rats

| Compound | Dose (mg/kg, p. o.) | No. of animals | Ulcer index (mm) | Inhibition (%) |
|---|---|---|---|---|
| 22[a] | 10 | 5 | 34.7 ± 8.4 | 62.7 |

[a]Reference compound (propentofylline)
**P < 0.01, *P < 0.05 (P = significance)
Each value represents the means ± S. E. (standard error)

2. TOXICOLOGICAL PROFILE

The oral $LC_{50}$ value of Compound 5 for mice was >2,500 mg/kg. The intravenous or intraperitoneal $LD_{50}$ values of the compounds of this invention and the reference compound (propentofylline) for mice are shown in Table 4.

TABLE 4

Acute intravenous or intraperitoneal toxicity of compounds involved in this invention in mice

| Compound No. | LD50 (mg/kg) | |
|---|---|---|
| 1 | 100–200 | (i.v.) |
| 2 | >200 | (i.v.) |
| 3 | >200 | (i.v.) |
| 4 | 100–200 | (i.v.) |
| 5 | >200 | (i.v.) |
| 6 | 150–300 | (i.p.) |
| 7 | >200 | (i.v.) |
| 8 | 100–200 | (i.v.) |
| 9 | >100 | (i.v.) |
| 10 | >200 | (i.v.) |
| 11 | 150–300 | (i.p.) |
| 12 | 300–600 | (i.p.) |
| 13 | >200 | (i.v.) |
| 14 | >200 | (i.v.) |
| 15 | >600 | (i.p.) |
| 16 | >200 | (i.v.) |
| 17 | >600 | (i.p.) |
| 18 | >200 | (i.v.) |
| 19 | >100 | (i.v.) |
| 20 | >100 | (i.v.) |
| 21 | — | |
| 22[a] | 107 (100–116) | (i.v.) |
| | 296 (272–323) | (i.p.) |

[a]Reference compound (propentofylline)

Examples of the invention will be as follows.

EXAMPLE 1

Production of 3,7-diethyl-1-(6-hydroxy-6-methylheptyl)-xanthine (Compound 13)

6.2 g of 3,7-diethylxanthine, 4.1 g of ptassium carbonate, and 6.6 g of 1-bromo-6-hydroxy-6-methylheptane are stirred in 100 ml of dimethylformamide at 120° C. for 18 hours. The mixture is filtered hot with suction, the filtrate is concentrated under recuced pressure final recrystallization from diisopropylether with addition of petroleum ether.

$C_{17}H_{28}N_4O_3$ (molecular weight=336.4).
Melting point: 82°–84° C.
Analysis: Calculated: C 60.69%, H 8.39%, N 16.65%.
Found: C 60.84%, H 8.46%, N 16.70%.

In an analogous manner to Example 1 the following compounds are obtained:

EXAMPLE 2

3-Ethyl-1-(6-hydroxy-6-methylheptyl)-7-propylxanthine (Compound 14)

This compound was prepared as described in Example 1 using 3-ethyl-7-propylxanthine as starting material.

$C_{18}H_{30}N_4O_3$ (MW=350.5).
Melting point: 62°–64° C.
Analysis: Calculated: C 61.69%, H 8.63%, N 15.99%.
Found: C 61.71%, H 8.85%, N 16.05%.

EXAMPLE 3

3-Ethyl-1-(6-hydroxy-6-methylheptyl)-7-isopropylxanthine (Compound 15)

This compound was synthesized starting from 3-ethyl-7-isopropylxanthine according to the procedure described in Example 1 and recrystallizing the final product from ethyl acetate.

$C_{18}H_{30}N_4O_3$ (MW=350.5).
Melting point: 104°–106° C.
Analysis: Calculated: C 61.69%, H 8.63%, N 15.99%.
Found: C 61.69%, H 8.77%, N 15.97%.

EXAMPLE 4

3,7-Diethyl-1-(5-hydroxy-5-methylhexyl)-xanthine (Compound 16)

This compound was obtained according to the method described in Example 1 starting from 3,7-diethylxanthine and 1-chloro-5-hydroxy-5-methylhexane and recrystallizing the final product from diisopropylether.

$C_{16}H_{26}N_4O_3$ (MW=322.4).
Melting point: 72°–73° C.
Analysis: Calculated: C 59.60%, H 8.13%, N 17.38%.
Found: C 59.58%, H 8.27%, N 17.48%.

EXAMPLE 5

7-Butyl-3-ethyl-1-(5-hydroxy-5-methylhexyl)-xanthine (Compound 17)

According to Example 1 7-butyl-3-ethylxanthine was reacted with 1-chloro-5-hydroxy-5-methylhexane; after isolation the final product was recrystallized from a mixture of ethyl acetate and petroleum ether.

$C_{18}H_{30}N_4O_3$ (MW=350.5).
Melting point: 56°–57° C.
Analysis: Calculated: C 61.69%, H 8.63%, N 15.99%.
Found: C 61.50%, H 8.76%, N 16.24%.

EXAMPLE 6

7-Allyl-3-ethyl-1-(5-hydroxy-5-methylhexyl)-xanthine (Compound 19)

This compound was prepared as described in Example 1 starting with 7-Allyl-3-ethyl-xanthine and 1-chloro-5-hydroxy-5-methylhexane and recrystallizing the final product from diisopropyl ether with addition of some ethyl acetate.

$C_{17}H_{26}N_4O_3$ (MW=334.4).
Melting point: 69°–70° C.
Analysis: Calculated: C 61.06%, H 7.84%, N 16.75%.
Found: C 60.92%, H 7.89%, N 16.81%.

EXAMPLE 7

7-Allyl-1-(5-hydroxy-5-methylhexyl)-3-methylxanthine (Compound 20)

This compound was obtained by reacting 7-Allyl-3-methylxanthine with 1-chloro-5-hydroxy-5-methylhexane in an analogous manner to Example 1.

$C_{16}H_{24}N_4O_3$ (MW=320.4).
Melting point: 67°–69° C.
Analysis: Calculated: C 59.98%, H 7.55%, N 17.49%.
Found: C 60.22%, H 7.66%, N 17.66%.

EXAMPLE 8

1-(3-Butenyl)-3-ethyl-7-(5-hydroxy-5-methylhexyl)-3-xanthine (Compound 21)

This compound was synthesized according to Example 1 starting with 3-ethyl-7-(5-hydroxy-5-methylhexyl)-xanthine and 1-bromo-3-butene. The final product was recrystallized from a mixture of ethyl acetate and petroleum ether.

$C_{18}H_{28}N_4O_3$ (MW=348.5).
Melting point: 53°–55° C.
Analysis: Calculated: C 62.04%, H 8.10%, N 16.08%.
Found: C 61.98%, H 8.29%, N 16.08%.

EXAMPLE 9

An injectable preparation was prepared as follows. Compound 2 (20 g) and sodium chloride (16 g) were added to distilled water for injection to make 2,000 ml. The solution was filtered through a 0.22 μm Millipore filter and divided at 5 ml into 5 ml ampules, which were sealed and sterilized in an autoclave.

EXAMPLE 10

Tablets each containing 115 mg of Compound 2 were prepared by a conventional method from a mixture of 500 g of Compound 2 with 250 g of lactose, 150 g of corn starch, 150 g of calcium carboxymethylcellulose, 42 g of talc, 5 g of magnesium stearate, and 3 g of silica. The tablets were coated with a suspension containing 500 ml of water, 40 g of hydroxypropylmethylcellulose, 2 g of polyethyleneglycol with the average molecular weight of 6,000, 3.5 g of titanium dioxide, and 3 g of talc.

EFFECTS OF INVENTION

As revealed by our studies described above, the compounds involved in this invention were shown to possess potent antiulcer effects and low toxicity. For example, Compound 2 is 2.5 times more effective than propentofylline in improving stress-induced gastric ulcers. The compounds involved in this invention other than Compound 2 also have same or more potent antiulcer effect than propentofylline.

What is claimed is:

1. A method for treating a patient suffering from peptic ulcer disease which comprises administering to said patient an effective amount of at least one compound represented by formula I

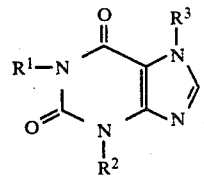

wherein one of $R^1$ and $R^3$ is

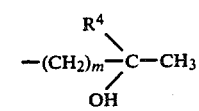

wherein m is 1–5, $R^4$ represents a $(C_1$–$C_4)$alkyl group; the other one of $R^1$ and $R^3$ is hydrogen, $(C_3$–$C_6)$alkenyl or $(C_1$–$C_8)$alkyl which can be substituted with up to 2 hydroxyl groups or a $(C_1$–$C_4)$alkoxy group; and $R^2$ is $(C_1$–$C_4)$alkyl.

2. The method of claim 1, wherein in formula I in which one of $R^1$ and $R^3$ denotes

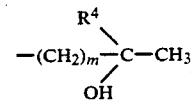

wherein m is 3, 4 or 5 and $R^4$ represents methyl or ethyl; the other one of $R^1$ and $R^3$ denotes hydrogen, $(C_3$–$C_4)$alkenyl or $(C_1$–$C_4)$alkyl optionally substituted with up to 2 hydroxyl groups or a $(C_1$–$C_2)$alkoxy group; and $R^2$ represents methyl or ethyl.

3. The method of claim 1, characterized in that in formula I in which one of $R^1$ and $R^3$ denotes

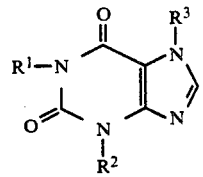

wherein
m is 4 or 5;
the other one of $R^1$ and $R^3$ represents $(C_1$–$C_4)$alkyl or is optionally substituted with a $(C_1$–$C_2)$alkoxy group and
$R^2$ is ethyl.

4. The method of claim 1, characterized in that in formula I in which $R^1$ denotes

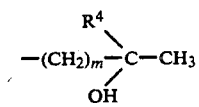

wherein
m is 4 or 5;
$R^3$ represents $(C_1$–$C_4)$alkyl or is optionally substituted with a $(C_1$–$C_2)$alkoxy group; and
$R^2$ is ethyl.

5. The method of claim 1, wherein $R^2$ denotes ethyl; and where a)
$R^1$ denotes 6-hydroxy-6-methylheptyl and R³ represents ethyl, propyl or isopropyl;

or b)

R¹ denotes 5-hydroxy-5-methylhexyl and

R³ represents ethyl or butyl.

6. The method of claim 1, wherein one of R¹ and R³ denotes

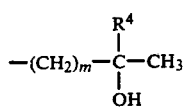

wherein m is an integer of 1-5 and R⁴ represents a $(C_1-C_4)$alkyl group;

the other one of R¹ and R³ denotes $(C_3-C_6)$alkenyl; and

R² represents $(C_1-C_4)$alkyl.

7. The method of claim 6, in which one of R¹ and R³ denotes

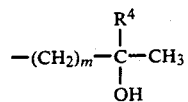

wherein m is an integer of 3, 4 or 5 and R⁴ represents methyl or ethyl;

the other one of R¹ and R³ denotes $(C_3-C_4)$alkenyl; and

R² represents methyl or ethyl.

8. The method of claim 6, in which one of R¹ and R³ denotes

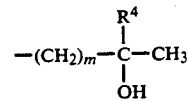

wherein m is an integer of 4 and R⁴ represents methyl; the other one of R¹ and R³ denotes allyl or butenyl; and R² represents methyl or ethyl.

9. The method of claim 1, further comprising combining said compound with a pharmaceutically acceptable carrier prior to administering said compound to said patient.

* * * * *

UNITED STATES PATENT AND TRADEMARK OFFICE
CERTIFICATE OF CORRECTION

PATENT NO. : 5,109,003
DATED : April 28, 1992
INVENTOR(S) : Toshizo Tanaka et al.

It is certified that error appears in the above-identified patent and that said Letters Patent is hereby corrected as shown below:

In claim 3, column 12, delete the formula " 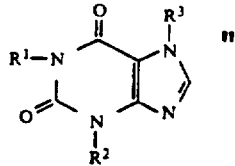 "

and insert therefor -- 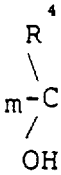 --.

Signed and Sealed this

Ninth Day of November, 1993

Attest:

BRUCE LEHMAN

Attesting Officer

Commissioner of Patents and Trademarks